(12) United States Patent
Axelsson et al.

(10) Patent No.: US 9,402,809 B2
(45) Date of Patent: Aug. 2, 2016

(54) SNUFF COMPOSITION

(75) Inventors: Anders Axelsson, Bjärred (SE); Arne Kristensen, Helsingborg (SE); Henri Hansson, Helsingborg (SE)

(73) Assignee: Niconovum USA, Inc., Winston Salem, NC (US)

( * ) Notice: Subject to any disclaimer, the term of this patent is extended or adjusted under 35 U.S.C. 154(b) by 1867 days.

(21) Appl. No.: 12/225,262

(22) PCT Filed: Mar. 16, 2007

(86) PCT No.: PCT/EP2007/002343
§ 371 (c)(1),
(2), (4) Date: Jun. 16, 2009

(87) PCT Pub. No.: WO2007/104573
PCT Pub. Date: Sep. 20, 2007

(65) Prior Publication Data
US 2009/0293895 A1    Dec. 3, 2009

Related U.S. Application Data

(60) Provisional application No. 60/782,903, filed on Mar. 16, 2006, provisional application No. 60/782,977, filed on Mar. 16, 2006.

(30) Foreign Application Priority Data

Mar. 16, 2006   (DK) .......................... PA 2006 00375
Mar. 16, 2006   (DK) .......................... PA 2006 00376

(51) Int. Cl.
*A24B 15/00*   (2006.01)
*A61K 9/00*   (2006.01)
(Continued)

(52) U.S. Cl.
CPC ............... *A61K 9/0056* (2013.01); *A24B 13/00* (2013.01); *A24B 15/14* (2013.01); *A61K 9/009* (2013.01); *A61K 31/465* (2013.01); *A61K 9/146* (2013.01)

(58) Field of Classification Search
None
See application file for complete search history.

(56) References Cited

U.S. PATENT DOCUMENTS 865,026 A    9/1907   Ellis
940,521 A    11/1909  Endicott
(Continued)

FOREIGN PATENT DOCUMENTS

CN    1089834    7/1994
CN    1383814    12/2002
(Continued)

OTHER PUBLICATIONS

Nasr et al., In Vitro Study of Nicotine Release from Smokeless Tobacco, Journal of AOAC International, vol. 81, No. 3, 1998.
(Continued)

*Primary Examiner* — Michael H Wilson
*Assistant Examiner* — Phu Nguyen
(74) *Attorney, Agent, or Firm* — Womble Carlyle Sandridge & Rice, LLP (57) ABSTRACT

Use of a nicotine-cellulose combination for the preparation of a snuff composition for achievement of a fast onset of action of nicotine after application of the snuff composition to the oral cavity of a subject, wherein the composition has a high release rate so that when subjected to an in vitro dissolution test about 45% or more of the total content of nicotine is released within 30 minutes. Moreover, the invention relates to an improved snuff composition for application to the oral cavity.

28 Claims, 8 Drawing Sheets

Sample tube (51) Int. Cl.
  A24B 13/00    (2006.01)
  A24B 15/14    (2006.01)
  A61K 31/465   (2006.01)
  A61K 9/14     (2006.01)

(56) References Cited

U.S. PATENT DOCUMENTS

| | | |
|---|---|---|
| 3,777,029 A | 12/1973 | Magid |
| 3,845,217 A | 10/1974 | Ferno et al. |
| 3,877,468 A | 4/1975 | Lichtneckert et al. |
| 3,901,248 A | 8/1975 | Lichtneckert et al. |
| 4,317,837 A | 3/1982 | Kehoe et al. |
| 4,579,858 A | 4/1986 | Ferno et al. |
| 4,593,572 A | 6/1986 | Linley, Jr. |
| 4,655,231 A | 4/1987 | Ray et al. |
| 4,674,491 A | 6/1987 | Brugger et al. |
| 4,696,315 A | 9/1987 | Summers |
| 4,806,356 A | 2/1989 | Shaw |
| 4,817,640 A | 4/1989 | Summers |
| 4,835,162 A | 5/1989 | Abood |
| 4,907,605 A | 3/1990 | Ray et al. |
| 4,933,188 A | 6/1990 | Cherukuri et al. |
| 4,945,929 A | 8/1990 | Egilmex et al. |
| 4,967,733 A | 11/1990 | Rousseau et al. |
| 4,967,773 A | 11/1990 | Shaw |
| 4,971,079 A | 11/1990 | Talapin et al. |
| 5,069,904 A | 12/1991 | Masterson |
| 5,077,104 A | 12/1991 | Hunt et al. |
| 5,135,753 A | 8/1992 | Baker et al. |
| 5,154,927 A | 10/1992 | Song et al. |
| 5,167,242 A | 12/1992 | Turner et al. |
| 5,198,226 A | 3/1993 | MacFarlane et al. |
| 5,268,209 A | 12/1993 | Hunt et al. |
| 5,284,163 A | 2/1994 | Knudsen et al. |
| 5,318,523 A | 6/1994 | Lu et al. |
| 5,326,570 A | 7/1994 | Rudnic et al. |
| 5,346,589 A | 9/1994 | Braunstein et al. |
| 5,362,496 A | 11/1994 | Baker et al. |
| 5,488,962 A | 2/1996 | Perfetti |
| 5,501,858 A | 3/1996 | Fuisz |
| 5,507,278 A | 4/1996 | Karell |
| 5,525,351 A | 6/1996 | Dam et al. |
| 5,543,424 A | 8/1996 | Carlsson et al. |
| 5,549,906 A | 8/1996 | Santus et al. |
| 5,573,774 A | 11/1996 | Keenan |
| 5,593,684 A | 1/1997 | Baker et al. |
| 5,599,554 A | 2/1997 | Majeti |
| 5,643,905 A | 7/1997 | Moormann et al. |
| 5,654,003 A | 8/1997 | Fuisz et al. |
| 5,656,255 A | 8/1997 | Jones |
| 5,662,920 A | 9/1997 | Santus |
| 5,692,493 A | 12/1997 | Weinstein et al. |
| 5,711,961 A | 1/1998 | Reiner et al. |
| 5,721,257 A | 2/1998 | Baker et al. |
| 5,733,574 A | 3/1998 | Dam et al. |
| 5,810,018 A | 9/1998 | Monte |
| 5,885,645 A | 3/1999 | Wong et al. |
| 5,935,604 A | 8/1999 | Illum |
| 5,939,100 A | 8/1999 | Albrechtsen et al. |
| 5,948,422 A | 9/1999 | van Koutrik et al. |
| 5,955,098 A | 9/1999 | Dugger, III |
| 6,024,981 A | 2/2000 | Khankari et al. |
| 6,062,214 A | 5/2000 | Howlett |
| 6,083,531 A | 7/2000 | Humbert-Droz et al. |
| 6,110,495 A | 8/2000 | Dam et al. |
| 6,129,936 A | 10/2000 | Gustafsson et al. |
| 6,183,775 B1 | 2/2001 | Ventouras |
| 6,190,696 B1 | 2/2001 | Groenewoud |
| 6,224,904 B1 | 5/2001 | Rapp et al. |
| 6,264,981 B1 | 7/2001 | Zhang et al. |
| 6,280,761 B1 | 8/2001 | Santus |
| 6,287,596 B1 | 9/2001 | Murakami et al. |
| 6,322,806 B1 | 11/2001 | Ream et al. |
| 6,322,828 B1 | 11/2001 | Athanikar et al. |
| 6,344,222 B1 | 2/2002 | Cherukuri et al. |
| 6,352,986 B1 | 3/2002 | Hassan et al. |
| 6,355,265 B1 | 3/2002 | Ream et al. |
| 6,358,060 B2 | 3/2002 | Pinney et al. |
| 6,358,527 B1 | 3/2002 | Gilis et al. |
| 6,426,090 B1 | 7/2002 | Ream et al. |
| 6,465,003 B2 | 10/2002 | Ream et al. |
| 6,551,634 B2 | 4/2003 | Joergensen |
| 6,558,692 B2 | 5/2003 | Ream et al. |
| 6,562,372 B1 | 5/2003 | Yokoi et al. |
| 6,586,023 B1 | 7/2003 | Song et al. |
| 6,599,901 B1 | 7/2003 | Flohr et al. |
| 6,602,518 B2 | 8/2003 | Seielstad et al. |
| 6,627,234 B1 | 9/2003 | Johnson et al. |
| 6,773,716 B2 | 8/2004 | Ream et al. |
| 6,790,496 B1 | 9/2004 | Levander et al. |
| 6,841,557 B2 | 1/2005 | Anderson et al. |
| 6,845,777 B2 | 1/2005 | Pera |
| 6,849,286 B1 | 2/2005 | Bayerköhler et al. |
| 6,849,624 B2 | 2/2005 | Ballard et al. |
| 6,855,820 B2 | 2/2005 | Broom et al. |
| 6,858,624 B2 | 2/2005 | Hagen et al. |
| 6,861,434 B2 | 3/2005 | Stack |
| 6,872,405 B2 | 3/2005 | Takaishi et al. |
| 6,893,654 B2 | 5/2005 | Pinney et al. |
| 6,932,971 B2 | 8/2005 | Bachmann et al. |
| 6,958,143 B2 | 10/2005 | Choi et al. |
| 6,958,323 B2 | 10/2005 | Olivera et al. |
| 6,960,574 B2 | 11/2005 | Prokai |
| 6,982,089 B2 | 1/2006 | Tobinick |
| 7,101,579 B2 | 9/2006 | Athanikar et al. |
| 7,163,705 B2 | 1/2007 | Johnson et al. |
| 7,208,186 B2 | 4/2007 | Norman et al. |
| 2001/0016593 A1 | 8/2001 | Wilheimsen |
| 2001/0029959 A1 | 10/2001 | Burgard et al. |
| 2002/0009523 A1 | 1/2002 | Gustaesson |
| 2002/0010198 A1 | 1/2002 | Jerussi et al. |
| 2002/0015687 A1 | 2/2002 | Bellamy et al. |
| 2003/0077297 A1 | 4/2003 | Chen et al. |
| 2003/0082109 A1 | 5/2003 | Gorenstein |
| 2003/0124191 A1 | 7/2003 | Besse et al. |
| 2003/0152634 A1 | 8/2003 | Bodmeier |
| 2003/0180360 A1 | 9/2003 | Am Ende et al. |
| 2003/0224048 A1 | 12/2003 | Walling |
| 2004/0013752 A1 | 1/2004 | Wolfson |
| 2004/0096501 A1 | 5/2004 | Vaya et al. |
| 2004/0191322 A1 | 9/2004 | Hansson |
| 2004/0194793 A1 | 10/2004 | Lindell et al. |
| 2004/0247669 A1 | 12/2004 | Gin et al. |
| 2005/0009813 A1 | 1/2005 | Moormann et al. |
| 2005/0009882 A1 | 1/2005 | Farr |
| 2005/0013856 A1 | 1/2005 | Trivedi et al. |
| 2005/0020641 A1 | 1/2005 | Sellers et al. |
| 2005/0042173 A1 | 2/2005 | Besse et al. |
| 2005/0053665 A1* | 3/2005 | Ek et al. ................. 424/488 |
| 2005/0058609 A1 | 3/2005 | Nazeri |
| 2005/0089524 A1 | 4/2005 | Sanderson et al. |
| 2005/0100513 A1 | 5/2005 | Watkins et al. |
| 2005/0107397 A1 | 5/2005 | Galambos et al. |
| 2005/0118272 A1 | 6/2005 | Besse et al. |
| 2005/0123502 A1 | 6/2005 | Chan et al. |
| 2005/0129774 A1 | 6/2005 | Morein et al. |
| 2005/0136047 A1 | 6/2005 | Ennifar et al. |
| 2005/0182063 A1 | 8/2005 | Yohannes |
| 2005/0197343 A1 | 9/2005 | Gmeiner et al. |
| 2005/0222270 A1 | 10/2005 | Olney et al. |
| 2005/0227998 A1 | 10/2005 | Voelker |
| 2005/0260264 A1 | 11/2005 | Edgren et al. |
| 2005/0261289 A1 | 11/2005 | Flohr et al. |
| 2005/0277626 A1 | 12/2005 | Dinan et al. |
| 2005/0282823 A1 | 12/2005 | Breining et al. |
| 2006/0057207 A1 | 3/2006 | Ziegler et al. |
| 2006/0058328 A1 | 3/2006 | Bhatti et al. |
| 2006/0062835 A1 | 3/2006 | Weil |
| 2006/0084656 A1 | 4/2006 | Ziegler et al. |
| 2006/0099300 A1 | 5/2006 | Andersen et al. |
| 2006/0147498 A1 | 7/2006 | Jonsson et al. |
| 2006/0165842 A1 | 7/2006 | Andersen et al. |
| 2006/0171969 A1 | 8/2006 | Macelloni et al. |
| 2006/0204451 A1 | 9/2006 | Salini |

(56) References Cited

U.S. PATENT DOCUMENTS

| | | |
|---|---|---|
| 2006/0240143 A1 | 10/2006 | Andersen et al. |
| 2006/0246174 A1 | 11/2006 | Andersen et al. |
| 2006/0252773 A1 | 11/2006 | Ceci |
| 2006/0275344 A1 | 12/2006 | Mody et al. |
| 2006/0276551 A1 | 12/2006 | Shytle et al. |
| 2007/0014887 A1 | 1/2007 | Cherukuri et al. |
| 2007/0071806 A1 | 3/2007 | McCarty |
| 2007/0134169 A1 | 6/2007 | Rabinoff |
| 2008/0020050 A1 | 1/2008 | Chau et al. |
| 2008/0124283 A1 | 5/2008 | Andersen |
| 2008/0131508 A1 | 6/2008 | Agarwal et al. |
| 2008/0138398 A1 | 6/2008 | Gonda |
| 2008/0138399 A1 | 6/2008 | Gonda |
| 2008/0138423 A1 | 6/2008 | Gonda |
| 2008/0286340 A1 | 11/2008 | Andersson et al. |
| 2008/0286341 A1 | 11/2008 | Andersson et al. |
| 2008/0292683 A1 | 11/2008 | Sanghvi et al. |
| 2008/0317863 A1 | 12/2008 | Nystrom et al. |
| 2009/0081291 A1 | 3/2009 | Gin et al. |
| 2009/0098192 A1 | 4/2009 | Fuisz |
| 2010/0004294 A1 | 1/2010 | Axelsson et al. |

FOREIGN PATENT DOCUMENTS

| | | |
|---|---|---|
| CN | 1511550 | 7/2004 |
| CN | 1557177 | 12/2004 |
| DE | 23 13 996 | 10/1974 |
| DE | 2313996 | 10/1974 |
| DE | 3241437 | 5/1984 |
| EP | 2 05 133 | 12/1986 |
| EP | 2 15 682 | 3/1987 |
| EP | 3 77 520 | 7/1990 |
| EP | 4 72 428 | 2/1992 |
| EP | 05 57 129 | 8/1993 |
| EP | 5 70 327 | 11/1993 |
| EP | 07 45 380 | 12/1996 |
| EP | 09 16 339 | 5/1999 |
| FR | 2147652 | 3/1973 |
| FR | 2467604 | 4/1981 |
| FR | 2 608 156 | 6/1988 |
| FR | 2698268 | 5/1994 |
| FR | 2788982 | 8/2000 |
| FR | 2792200 | 10/2000 |
| GB | 1528391 | 10/1978 |
| GB | 2030862 | 4/1980 |
| GB | 2 227 659 | 8/1990 |
| GB | 2255892 | 11/1992 |
| GB | 2289204 | 11/1995 |
| GB | 2308992 | 7/1997 |
| GB | 2 393 392 A | 3/2004 |
| GB | 2393392 | 3/2004 |
| JP | 2005/082587 | 3/2005 |
| JP | 2005103113 | 4/2005 |
| JP | 2005320342 | 11/2005 |
| RU | 2029474 | 2/1995 |
| SU | 1232260 | 5/1986 |
| SU | 1268141 | 11/1986 |
| WO | WO 88/03803 | 6/1988 |
| WO | WO91/01132 | 2/1991 |
| WO | WO91/04757 | 4/1991 |
| WO | WO91/06288 | 5/1991 |
| WO | WO91/09599 | 7/1991 |
| WO | WO91/09731 | 7/1991 |
| WO | WO95/03050 | 2/1995 |
| WO | WO95/20411 | 8/1995 |
| WO | WO97/02273 | 1/1997 |
| WO | WO97/10162 | 3/1997 |
| WO | WO97/42941 | 11/1997 |
| WO | WO99/15171 | 4/1999 |
| WO | WO99/65550 | 12/1999 |
| WO | WO00/19977 | 4/2000 |
| WO | WO00/38686 | 7/2000 |
| WO | WO00/45795 | 8/2000 |
| WO | WO00/56281 | 9/2000 |
| WO | WO01/37814 | 5/2001 |
| WO | WO02/102357 | 12/2002 |
| WO | WO03/013719 | 2/2003 |
| WO | WO03/002446 | 7/2003 |
| WO | WO03/053175 | 7/2003 |
| WO | WO-03/053175 A2 | 7/2003 |
| WO | WO03/055486 | 7/2003 |
| WO | WO03/061399 | 7/2003 |
| WO | WO03/101454 | 12/2003 |
| WO | WO 2004/004480 | 1/2004 |
| WO | WO 2004/056219 | 7/2004 |
| WO | WO-2004/056219 A | 7/2004 |
| WO | WO 2004/056363 | 7/2004 |
| WO | WO-2004/056363 | 7/2004 |
| WO | WO 2004/064811 | 8/2004 |
| WO | WO-2004/064811 | 8/2004 |
| WO | WO-2005/023227 | 3/2005 |
| WO | WO 2005/034968 | 4/2005 |
| WO | WO 2005/040338 | 5/2005 |
| WO | WO 2005/053691 | 6/2005 |
| WO | WO 2005/115180 | 12/2005 |
| WO | WO-2005/115180 | 12/2005 |
| WO | WO 2006/028344 | 3/2006 |
| WO | WO 2006/037418 | 4/2006 |
| WO | WO 2006/115202 | 11/2006 |
| WO | WO 2007/006117 | 1/2007 |

OTHER PUBLICATIONS

European Board of Appeal Decision of Technical Board: "*Interlocutory Decision of the Opposition Division of the European Patent Office Posted on Jul. 12, 2010 Concerning Maintenance of the European U.S. Pat. No. 1578422 in Amended Form,*" Decision dated Jan. 27, 2015. pp. 1-31.

Ullman's Encyclopedia of Industrial Chemistry, $5^{th}$ Revised Ed. (1991), vol. A 19, Ed. Elvers, B., Hawkins, S. and Schulz, G.

http://www.fmc.com/—pages for Avicel products and MCC/Cellulose gel.

http://en.wikipedia.mg/wiki/Excipient.

Axelsson et al., "The Anti-smoking Effect of chewing gum with nicotine of high and low bioavailability"; 3rd World Conference on Smoking and Health, New York, 1975.

Jenkusky, "Use of Nicotine Patches for Schizophrenic Patients," *Am J. Psychiatry*, 150:12, Dec. 1993. P. 1899.

Lihong et al., "Preparation and Pharmaceutical Study of Nicotine Sustained Release Tablet," *The Journal of Pharmaceutical Practice*, vol. 19, 2001, No. 4, pp. 288-289.

Mihranyan et al., "Sorption of nicotine to cellulose powders", European Journal Pharmaceutical Sciences; 2004; 279-286; 22(4).

Mihranyan, "Engineering of Native Cellulose Structure for Pharmaceutical Applications, Influence of Cellulose Crystallinity Index, Surgace Area and Pore Volume on Sorption Phenomena", ACTA Universitatis Upsaliensis Uppsala; 2005; 1-57.

Molander el al., "Pharmacokinetic investigation of a nicotine sublingual tablet", .Eur. J. Clin. Pharmacol. 2001; 813-9; vol. 56(11).

Morjaria et al., "In Vitro Release of Nicotine From Chewing Gum Formulations", Dissolution Technologies; May 2004; 12-15; vol. 11(2).

Nasr et al., "In Vitro Study of Nicotine Release From Smokeless Tobacco," *J. AOAC International*, 1998, vol. 81, No. 3. pp. 540-543.

Thomas et al., "Transdermal Nicotine ad Maintenance Therapy for Ulcerative Colitis," *The New England Journal of Medicine*, Apr. 13, 1995.

Quik, "Smoking, Nicotine and Parkinson's Disease," *Trends in Neurosciences*, vol. 27, No. 9, 2004.

Sahakian et al., "Nicotine and Tetrahydroaminoacradine: Evidence for Improved Attention in Patients and Dementia of the Alzheimer Type," Dept. of Experimental Psychology, University of Cambridge, U.K. *Drug Development Research*, vol. 31, pp. 80-88, 1994.

\* cited by examiner

Assembly of the membrane to the silicone hose

Fig. 1

Overview of tubing routes

SNUFF COMPOSITION

FIELD OF THE INVENTION

The present invention relates to the use of a nicotine-cellulose combination for the preparation of a snuff composition for achievement of a fast onset of action of nicotine after application of the snuff composition to the oral cavity of a subject, wherein the composition has a high release rate so that when subjected to an in vitro dissolution test about 45% or more of the total content of nicotine is released within 30 minutes. Moreover, the invention relates to an improved snuff composition for application to the oral cavity.

BACKGROUND OF THE INVENTION

Wet snuff is a variant of nicotine addition mainly seen in the US and Scandinavia and particularly in Sweden, where this variant is used on a daily basis by approximately 20% of men.

Although wet snuff is not implicated in the cardiovascular and lung disease morbidity and mortality caused by smoking, the content of nitrosamines poses a potential hazard for some cancer diseases. It is therefore of interest to make available to consumers a snuff-like product while minimising this potential hazard.

The vascular area at the administration route and the fact that the snuff is fixed over a long period of time gives an opportunity for both a quick and thorough uptake of nicotine over the mucosa. To develop a new medicated snuff bag—Snuff Similar—with similar nicotine effects but without the carcinogenic risks derived from the tobacco was the objective for this project. To reach other countries in Europe and worldwide, one approach would be to have a product that is more clean and more socially acceptable in its appearance. By using the white cellulose complex this could be achieved. A more socially acceptable alternative might also potentially increase usage, especially among women.

Due to the slow wetting and thereby release, migration and absorption of nicotine, nicotine release from snuff bags is incomplete in vivo. A present snuff variant on the market is "General white" (Swedish Match AB), has a loaded amount of 8.0 mg nicotine per snuff bag and an approximate in vitro release of 1.4 mg over a period of 30 minutes. The release in vivo is consequently less than 20%. This is mainly due to the low amount of saliva available to dissolve the nicotine and to the fact that the snuff bag is kept in place over the time of administration. Accordingly, in order to load as little nicotine as possible, there is a need for snuff bag compositions, which have a higher total release of nicotine. This will also imply that less nicotine is used in the method for preparation of such snuff compositions, which is also beneficial from an economic and an environmental point of view.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

The present invention relates to the use of a nicotine-cellulose combination for the preparation of a snuff composition for achievement of a fast onset of action of nicotine after application of the snuff composition to the oral cavity of a subject. The composition has a high release rate so that when subjected to an in vitro dissolution test about 45% or more of the total content of nicotine is released within 30 minutes.

In general the onset of the nicotine effect is within 5 minutes such as, e.g. within 4 minutes, within 3 minutes, within 2 minutes or within 1.5 minutes after application of composition between the lip and the teeth of a subject.

In the present context the term "nicotine-cellulose combination" is intended to denote a solid material composed of a cellulose which has sorbed (adsorbed and/or absorbed) a well-defined amount of nicotine (either as free base or as a pharmaceutically acceptable salt, complex or solvate) e.g. in voids or pores within the cellulose. The terms "nicotine-cellulose adduct" and "nicotine-cellulose carrier complex" as used herein are intended to have the same meaning as the term "nicotine-cellulose combination". As used herein cellulose is an example of a carrier.

In WO 2004/056363 (to the same Applicant) is described such a nicotine-cellulose combination for release of nicotine. However, there is no disclosure of the use of such a material for the preparation of a snuff composition for use in the oral cavity.

Moreover, the present inventors have found that the use of such a nicotine-cellulose combination is especially suitable for use in a snuff composition as such a snuff composition, on the one hand releases nicotine relatively fast and thereby enables a fast onset of the nicotine effect, and on the other hand enables the nicotine content in the snuff composition to be completely or almost completely released after application in the oral cavity. The complete or almost complete release is also seen after encapsulating of the snuff composition in a suitable bag, pouch or membrane. The bag or pouch may be of any suitable material e.g. wowen or non-wowen fabric (e.g. cotton, fleece etc.), heat sealable non-wowen cellulose or other polymeric materials such as a synthetic, semi-synthetic or natural polymeric material as described herein. A material suitable for use must provide a semi-permeable membrane layer to prevent the powder or composition from leaving the bag or pouch during use. Suitable materials are also those that do not have a significant impact on the release of nicotine from the composition. To the best of the inventor's knowledge, the nicotine/tobacco snuff products available on the market today only releases a part of the nicotine contained in the snuff product (see the Examples herein).

The snuff is normally in the form of a bag or pouch suitable for buccal administration (e.g. to be inserted between the lip and the teeth) and the bag or pouch comprises the nicotine in the form of a nicotine-cellulose combination. In a particular interesting embodiment; the cellulose is microcrystalline cellulose having a mean particle size of about 180 μm. An example of a suitable quality is e.g. Avicel PH-200.

The snuff composition according to the present invention may also comprise one or more pharmaceutically acceptable excipients or additives that are suitable for buccal administration. Such agents include—but are not limited to—fillers, binders, wetting agents, stabilizing agents, coloring agents, surface active agents, pH adjusting agents, absorption enhancers, taste-masking agents, flavoring agents, texture-improving agents, etc.

As indicated above, in a specific embodiment of the present invention, the nicotine-cellulose combination (normally together with one or more pharmaceutically acceptable excipients or additives) is enclosed in a membrane material. The membrane may be a natural, synthetic, semi-synthetic hydrophilic or hydrophobic membrane. It may be made from one or more biocompatible and physiologically acceptable polymeric material. Examples of suitable membrane materials are cellulose acetate and derivatives thereof, carboxymethyl cellulose, polycellulose ester, other cellulose derivatives including ethylcellulose, propylcellulose, polyethylene, polypropylene, polystyrene, polyvinyl chloride, polyvinyl acetate, polymers of methacrylates and acrylates, natural rubber, polycarbonate, polyethylene terephthalate, polyester, polyamide and nylon. Other suitable materials are mentioned herein before.

In keeping with long-standing patent law convention, the words "a" and "an" when used in the present specification in concert with the word comprising, including the claims, denote "one or more." As used herein "another" may mean at least a second or more. Some embodiments of the invention may consist of or consist essentially of one or more elements, method steps, and/or methods of the invention. It is contemplated that any method or composition described herein can be implemented with respect to any other method or composition described herein.

In one aspect, the invention relates to a snuff composition for buccal administration in the cheek pouch between the cheek and the jaw or under the lip. The composition may include tobacco.

The use of tobacco is deeply rooted in a large part of the world population. In the Scandinavian countries and in particular Sweden the use of moist snuff (snus) is very common as an alternative to smoking. Snuff is fermented and milled/grinded tobacco with a relatively large water content (40-60% w/w), normally to be used under the front upper lip of a human being.

Tobacco itself varies somewhat in nicotine content due to its natural origin. To adjust the nicotine release in moist snuff, various buffer systems may be added, e.g. carbonates. The moist snuff is either packed loosely, as bulk in a box or as single doses in small non-woven bags. A number of the filled and sealed bags are then packed in a box.

The moist snuff as a single dose has become popular due to the ease of use compared to the bulk product. The popularity of moist snuff is most probably due to its pharmacological nicotine absorption profile. The dose of nicotine and speed of absorption is approximately 10 ng per ml over 10 minutes though this may vary between brands. Measurements of plasma nicotine concentrations after a single day of moist snuff consumption also yielded levels similar to cigarette use. The kinetics are slightly slower compared to the kinetics when smoking tobacco, such as e.g. cigarettes and cigars; however, the overall amount of nicotine absorbed is higher when snuff is employed.

A snuff composition according to the invention comprises nicotine, or a pharmaceutically acceptable salt, solvate, complex, adduct, or derivative thereof, wherein—and when subjected to an in vitro dissolution test as described herein for 30 minutes about 30% or more of the total content of nicotine is released. This requirement with respect to in vitro release ensures that a sufficient amount of nicotine is rapidly available for absorption through the oral mucosa. In particular embodiments, about 35% or more such as, e.g., about 40% or more, about 42% or more, about 45% or more, about 50% or more of the total content of nicotine is released. In embodiments of particular interest, the release of nicotine is about 45% or more of the total content of nicotine within 30 minutes (in an in vitro test). Notably, the release within this period of time is about 50% or more such as, e.g., about 60% or more, about 70% or more or about 75% or more of the total content of nicotine in the snuff composition. The same applies to snuff compositions encapsulated in a polymeric membrane as described herein.

One important feature of the present invention is that the snuff composition leads to a rapid appearance of nicotine in the plasma. Accordingly, in general the in vivo uptake of nicotine 30 minutes after buccal administration corresponds to at least about 30% of the total content of nicotine in the snuff. As seen from the examples herein the snuff composition can be formulated so that the in vivo release of nicotine 30 minutes after buccal administration is higher, i.e. it corresponds to at least about 35% such as, e.g., at least about 40%, at least about 42%, at least about 45%, at least about 50%, at least about 55%, at least about 60%, at least about 65%, at least about 70% or at least about 75% of the total content of nicotine in the snuff.

In a specific embodiment a snuff composition according to the invention comprises a carrier comprising internal voids. Such voids may at least partially comprise said nicotine. The carrier is typically insoluble in water or has a low solubility in water. Thus, it typically has a solubility in water at room temperature of less than 1% w/w.

A particular suitable carrier for use in a snuff composition of the invention is a cellulose, such as a microcrystalline cellulose ("mcc"). The cellulose may be synthetic or semi-synthetic celluloses, or it may be derived from natural celluloses. It is normally crystalline such as microcrystalline. Certain specific embodiments may also utilize other forms of carriers, in addition to or including mcc, such as but not limited to fibrous material or carbohydrates including cellulose (including hemicellulose, celluloses with different crystallinities and structures (e.g., varying structures including solid fibers, and addition or including fibers or the like in various structures such as web-like structures and/or other structures), including naturally occurring celluloses including *Cladophora* sp. Algae cellulose or the like), dextran, agarose, agar, pectin, alginate, xanthan, chitosan, starch (including potato starch, shoti starch) etc. or mixtures thereof. While not intended to be bound by theory, it is believed as of the time of this patent application that nicotine may interact the carrier (for example, mcc or other suitable carrier including other cellulose carriers) by absorbing into and/or adsorbing onto the carrier. Such interaction is completely or nearly completely reversible.

The microcrystalline cellulose may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof.

Suitable carriers may also be those disclosed in WO 2004/064811, which is hereby included by reference.

More specifically, it is contemplated that a relatively high surface area may be of importance for a carrier that is suitable for use. Accordingly, the specific surface area of suitable carriers is normally at least 0.7 $m^2/g$ such as, e.g., 1 $m^2/g$. In certain uses the specific surface area may range between about 0.7 $m^2/g$ and at least about 100 $m^2/g$ and/or may be anything within this range and/or may be any mixture of sizes within this range. For example, in certain embodiments, the surface area may be about 0.7 $m^2/g$, about 1 $m^2/g$, about 1.5 $m^2/g$, about 2.0 $m^2/g$, about 3.0 $m^2/g$, about 5 $m^2/g$, about 7 $m^2/g$, about 10 $m^2/g$, about 15 $m^2/g$, about 20 $m^2/g$, about 25 $m^2/g$, about 35 $m^2/g$, about 45 $m^2/g$, about 50 $m^2/g$, about 75 $m^2/g$, about 100 $m^2/g$ and above about 100 $m^2/g$, or combinations thereof. Such carriers having such suitable surface areas may include, but are not limited to, mcc, fibrous material or carbohydrates including cellulose (including hemicellulose, celluloses with different crystallinities and structures (e.g., varying structures including solid fibers, and addition or including fibers or the like in various structures such as weblike structures and/or other structures), including naturally occurring celluloses including *Cladophora* sp. Algae cellulose or the like), dextran, agarose, agar, pectin, alginate, xanthan, chitosan, starch (including potato starch, shoti starch) etc. and/or mixtures thereof.

In a specific embodiment, nicotine is sorbed on microcrystalline cellulose.

In general, the mean particle size of the carrier such as microcrystalline cellulose is one that is not too low and neither too high such as, e.g., at the most about 500 µm, at the most about 450 µm, at the most about 300 µm, or at the most about 200 µm, or from about 5 to about 500 µm, from 10 to about 500 µm, from 15 to about 500 µm, from about 20 to about 500 µm, from about 30 to about 500 µm, from about 40 to about 500 µm, from about 10 to about 400 µm, from about 20 to about 400 µm, from about 30 to about 400 µm, from about 40 to about 400 µm, from about 30 to about 300 µm, from about 40 to about 300 µm, from about 50 to about 250 µm, from about 50 to about 200 µm or from about 75 to about 200 µm. In specific embodiments the particle size used were about 100 µm. In a preferred aspect, the mean particle size is in a range of from about 15 to about 250 µm such as from about 20 to about 200 µm. In the examples herein a quality of microcrystalline cellulose having a mean particle size of 180 µm has proved to be well-suited for the present purpose.

In a preferred embodiment a snuff composition according to the invention contains nicotine as a nicotine-microcrystalline cellulose carrier complex in which said nicotine is at least partly sorbed on microcrystalline cellulose and/or is at least partially absorbed into the carrier and/or is at least partially adsorbed onto the carrier (e.g., mcc), or mixtures thereof. Such interaction is completely or nearly completely reversible Hence, in certain specific embodiments nicotine is sorbed on microcrystalline cellulose, absorbed into the mcc and/or adsorbed onto the mcc, and/or combinations thereof.

In embodiments of the present invention, the carrier (e.g., but not limited to mcc and/or other naturally-occurring cellulose) is at least partially porous. This porosity may be due, for example but not limited to, the structure of the carrier, for example, branched, fibrous, or weblike structures may have pores. Ranges of pore sizes include but are not limited to pore volumes of about 0.01 $cm^3/g$ and include, but are not necessarily limited to pore volume ranges of from about 0.003 $cm^3/g$ or less to about 0.025 $cm^3/g$, to about or greater than 0.60 $cm^3/g$.

In general, the nicotine carrier complex or nicotine carrier adduct is present in a snuff composition of the invention in a concentration of at least about 2% w/w such as in a range from about 2% w/w to about 98% w/w, from about 2% to about 96% w/w, from about 2% w/w to about 95% w/w, from about 3% w/w to about 90% w/w, from about 4% w/w to about 85% w/w, from about 5% w/w to about 80% w/w, from about 5% w/w to about 75% w/w, from about 5% w/w to about 70% w/w, or from about 7.5% w/w to about 65% w/w.

In certain embodiments, the amount of nicotine sorbed, for example absorbed into and/or adsorbed onto to carrier can be up to 50% or more of the total weight of the composition. Ranges of the amount of nicotine sorbed onto the carrier in the present invention range for less than about 1% of the total weight of the composition to more than about 50% of the composition, including all amounts within this range. While applicants do not intend the invention to be bound by theory, it is believed at the time of preparing this application that the maximum amount of nicotine that can be sorbed onto and/or into the carrier, thereby affecting the amount, for example the percent nicotine by weight of the total composition (e.g., the maximum percentage) is affected by properties of the carrier, including but not limited to the structure of the carrier, the porosity of the carrier, and the surface area of the carrier.

In certain embodiments, the concentration of the nicotine carrier complex or nicotine carrier adduct in a composition of the invention is present in a concentration such as, e.g., from about 80% w/w to about 98% w/w, such as, e.g., from about 85% w/w to about 98% w/w, from about 90% w/w to about 98% w/w, from about 92% w/w to about 98% w/w, from about 93% w/w to about 97% w/w or from about 94% w/w to about 96% w/w.

In an alternative embodiment, the carrier compound is capable of forming a complex with nicotine such as, e.g., in the case that the carrier compound is an ion-exchange compound including polacrilex.

Concentrations and Amounts of Nicotine

As mentioned above, nicotine may be present in any suitable form. Normally, nicotine is selected from the group consisting of nicotine base, nicotine hydrochloride, nicotine dihydrochloride, nicotine monotartrate, nicotine bitartrate, nicotine sulfate, nicotine zinc chloride such as nicotine zinc chloride monohydrate and nicotine salicylate. In a preferred aspect, nicotine is in its free base form, which easily can be sorbed on a cellulose to form a microcrystalline cellulose-nicotine carrier complex or carrier adduct.

Normally, the nicotine compound (calculated as the free base) is present in a concentration of at least about 0.1% w/w such as in a range from about 0.1% w/w to about 50% w/w such as, e.g., from about 0.5% w/w to about 45% w/w, from about 1.0% w/w to about 40% w/w, from about 1.5% w/w to about 35% w/w, from about 2% w/w to about 30% w/w, from about 2.5% w/w to about 25% w/w, from about 2.5% w/w to about 20% w/w, from about 3% w/w to about 15% w/w.

However, in a more interesting embodiment a snuff composition according to the invention contains nicotine in a concentration from about 0.1% w/w to about 10% w/w, such as, e.g., from about from about 0.1% w/w to about 8% w/w, from about 0.1% w/w to about 6% w/w, from about 0.1% w/w to about 4% w/w, from about 0.1% w/w to about 2% w/w, from about 0.1% w/w to about 1.5% w/w, from about 0.2% w/w to about 1.0% w/w or from about 0.2% w/w to about 0.8% w/w, calculated as free base.

In a snuff composition of the invention the nicotine is typically present in a concentration from about 0.1% w/w to about 5% w/w, such as, e.g., from about from about 0.1% w/w to about 4% w/w, from about 0.1% w/w to about 3% w/w, from about 0.1% w/w to about 2% w/w, from about 0.1% w/w to about 1% w/w, from about 0.1% w/w to about 0.75% w/w, from about 0.2% w/w to about 0.5% w/w or from about 0.2% w/w to about 0.4% w/w, calculated as free base.

As mentioned above, the nicotine is present in the form of a nicotine-cellulose combination. In general, this combination is present in a concentration of from about 5% to about 100% such as, e.g., from about 10 to about 100%, from about 5% to about 50% or, alternatively, from about 45% to about 100%. The choice of suitable concentration depends on the load of nicotine in the nicotine-cellulose combination and the dosage of nicotine in a single pouch or bag. If the load is relatively high, then the concentration of the combination may be lower than if the load is relatively low. In a specific embodiment using e.g. Avicel® or a similar cellulose quality a concentration of the combination is generally from about 80% w/w to about 98% w/w, such as, e.g., from about 85% w/w to about 98% w/w, from about 90% w/w to about 98% w/w, from about 92% w/w to about 98% w/w, from about 93% w/w to about 97% w/w or from about 94% w/w to about 96% w/w.

The concentration of nicotine (or the pharmaceutically acceptable salt, complex or solvate thereof in the combination is at the most 70% w/w such as, e.g., at the most 60% w/w, at the most 50% w/w, at the most 45% w/w. The content of nicotine must not be so high that the combination (which is in powder form) "sweats", so that nicotine desorbs, evaporates or otherwise disappears from the combination. Accordingly, the load of nicotine in the combination is dependent on the particular cellulose employed. If the surface area of the cellulose material is relatively high, then a larger amount of nicotine can be contained therein in a stable manner during a suitable period of time, whereas a cellulose having a smaller surface area normally is indicative for a lower capacity to load nicotine in a suitable manner with respect to stability.

For most cellulose qualities, the concentration of nicotine in the nicotine-cellulose combination is at the most about 45% w/w, such as, e.g., at the most about 40% w/w, at the most about 35% w/w, at the most about 30% w/w, at the most about 25% w/w, at the most about 20% w/w, at the most about 15% w/w, at the most about 12.5% w/w, at the most about 10% w/w, at the most about 9.5% w/w, at the most about 9% w/w, at the most about 8.5% w/w or at the most about 8% w/w, and the concentration being calculated as the nicotine base.

In a specific embodiment, a particulate material according to the present invention has a concentration of nicotine or the pharmaceutically acceptable salt, complex or solvate thereof in the particulate material is at the most about 7.5% w/w such as, e.g., at the most about 7% w/w, at the most about 6.5% w/w, at the most about 6% w/w, at the most about 5.5% w/w, at the most about 5% w/w, at the most about 4.5% w/w, at the most about 4% w/w, at the most about 3% w/w, at the most about 2% w/w or at the most about 1% w/w, and the concentration being calculated as the nicotine base.

The amount of the nicotine compound (calculated as the free base) in a composition of the inventions is generally from about 0.5 mg to about 10 mg such as, e.g., from about 1 mg to about 8 mg, from about 1.5 mg to about 7.5 mg, from about 2 mg to about 5 mg, from about 2.5 mg to about 5 mg, from about 3 to about 10 mg, from about 3 to about 7.5 mg or from about 3 mg to about 5 mg such as, e.g., about 1.5 mg, about 2 mg, about 2.5 mg, about 3 mg, about 3.5 mg, about 4 mg, about 5 mg or about 6 mg, as calculated as free nicotine base. In particular a dosage of 2 mg, 3 mg, 4 mg and 6 mg is of commercial interest.

Buffering Agents

A composition according to the invention may also contain one or more buffering agents. It is generally known that a slightly alkaline reaction (between 7 and 8) in the oral cavity enhances the absorption of nicotine. Accordingly, it may be and advantage to incorporate a buffer substance in the composition such that a slightly alkaline reaction is provided. Especially compositions for release of the nicotine in the oral cavity can advantageously contain a buffer substance, i.e. compositions like snuff compositions.

Suitable buffering agents are typically those selected from the group consisting of acetates, glycinates, phosphates, glycerophosphates, citrates such as citrates of alkaline metals, carbonates, and hydrogen carbonates, and borates, or mixtures thereof. Especially, a carbonate, a hydrogen carbonate or a phosphate including a triphosphate is suitable as a buffer agent.

If present the one or more buffering agents are present in a concentration from about 0.5% w/w to about 5% w/w, such as, e.g., from about 0.75% w/w to about 4%, w/w, from about 0.75% w/w to about 3%, w/w or from about 1% w/w to about 2%, w/w.

In a specific embodiment, the concentration of the one or more buffering agents is from about 0.1% w/w to about 5% w/w, such as, e.g., from about 0.2% w/w to about 4% w/w, from about 0.3% w/w to about 4% w/w, from about 0.4% w/w to about 3% w/w, from about 0.5% w/w to about 2% w/w, from about 0.6% w/w to about 1% w/w or from about 0.7% w/w to about 0.9% w/w such as about 0.8% w/w.

Sweeteners—Flavouring Agents

In order to improve the sensory properties of the composition according to the invention one or more sweeteners or texture improves may be added, such as sugar alcohols including xylitol, sorbitol, maltitol and/or isomalt, or artificial sweeteners such as e.g. aspartame, acesulfame or saccharin.

The concentration of the one or more sweeteners, if present, is normally at least about 0.05% such as, e.g. from about 0.075% w/w to about 5% w/w or from about 5% to about 35% w/w, such as, e.g., from about 10% w/w to about 35% w/w, from about 15% w/w to about 35% w/w or from about 20% w/w to about 30% w/w. In an interesting embodiment the one or more sweeteners are present in a concentration from about 0.01% w/w to about 0.2% w/w, such as, e.g., from about 0.01% w/w to about 0.15% w/w, from about 0.02% w/w to about 0.12% w/w, from about 0.03% w/w to about 0.11% w/w, from about 0.04% w/w to about 0.1% w/w, from about 0.05% w/w to about 0.1% w/w, from about 0.06% w/w to about 0.1% w/w or from about 0.07% w/w to about 0.09% w/w such as about 0.08% w/w. As demonstrated in the examples herein a concentration of the one or more artificial sweeteners of about 0.08% gives good sensoric acceptance.

In order to improve the organoleptic properties of a composition according to the invention, the composition may include one or more flavouring agents, such as, e.g., menthol flavour, eucalyptus, mint flavour and/or L-menthol, normally present (total concentration of flavouring agents) in a concentration of from about 0.5% w/w to about 12% w/w, from about 1% w/w to about 10% w/w, from about 1.5% w/w to about 9% w/w or from about 2% w/w to about 8% w/w.

In a particular embodiment the flavour is mint flavour and the concentration of the one or more flavouring agents is from about 1% w/w to about 15% w/w, such as, e.g., from about 1% w/w to about 10% w/w, from about 1.5% w/w to about 8% w/w, from about 2% w/w to about 6% w/w or from about 3% w/w to about 5% w/w such as about 4% w/w. In a specific embodiment, the concentration of the one or more flavouring agents is about 4% w/w.

It is well-known that nicotine is subject to oxidation and accordingly, it may be advantageous to incorporate one or more anti-oxidants, such as, e.g., ascorbyl palmitate and/or sodium ascorbate, in a composition according to the invention.

The one or more anti-oxidants may be present in a concentration of from about 0.4% w/w to about 2.4% w/w, such as, e.g., from about 0.5% w/w to about 2.2% w/w, from about 0.6% w/w to about 2% w/w, from about 0.7% w/w to about 1.8% w/w or from about 0.8% w/w to about 1.6% w/w.

Specific Embodiments

In specific embodiments the invention relates to

A snuff composition comprising
i) a carrier,
ii) nicotine, or a pharmaceutically acceptable salt, solvate, complex, or derivative thereof,
wherein at least about 30% w/w of the total content of nicotine is released within 30 minutes when said composition is subjected to an in vitro dissolution test.

A snuff composition comprising
i) a nicotine-cellulose combination
ii) one or more pharmaceutically acceptable excipients or additive
the composition being encapsulated in a bag, pouch or membrane material.

A snuff composition comprising
i) a nicotine-cellulose combination containing from about 0.5 to about 10 mg of nicotine
ii) a flavoring agent
iii) a sweetener
the composition being encapsulated in a bag, pouch or membrane material.

A snuff composition comprising
i) a nicotine-cellulose combination containing from about 0.5 to about 10 mg of nicotine
ii) a flavoring agent
iii) a sweetener
iv) an antioxidant
the composition being encapsulated in a bag, pouch or membrane material.

A method of administering a snuff composition with a high release rate comprising the step of:
delivering a snuff composition comprising a carrier combined with nicotine, or a pharmaceutically acceptable salt, solvate, complex, or derivative thereof, wherein at least about 30% w/w of the total content of nicotine is released within 30 minutes when said composition is subjected to an in vitro dissolution test.

A method of making a snuff composition with a high release rate, comprising the step of: combining nicotine, or a pharmaceutically acceptable salt, solvate, complex, or derivative thereof, with a carrier, wherein at least about 30% w/w of the total content of nicotine is released within 30 minutes when said composition is subjected to an in vitro dissolution test.

All particulars and details mentioned above relating to the main aspect in general apply mutatis mutandis to the above mentioned specific embodiments.

The invention is further illustrated in the following figures and non-limiting examples.

METHODS

In vitro Dissolution Test

The snuff compositions according to the invention are normally tested to fulfill specific requirements with respect to in vitro release of nicotine. A suitable in vitro test depends on the specific composition in question. In general, a person skilled in the art will find guidance as to how to choose a relevant dissolution test for a specific composition in the official monographs such as, e.g., the European Pharmacopoeia. Below are described suitable dissolution tests in case of snuff compositions.

Snuff

The following dissolution method for testing of the release of nicotine from snuff compositions was used.

The method describes in-vitro release of nicotine from snuff using UV detection. The released nicotine diffuses through a dialysis membrane into a stream of tempered phosphate buffer.

Equipment

| UV spectrophotometer | HP 8453 or equivalent |
| Sipper | HP Peristaltic pump or equivalent |
| Secondary pump | Flexicon PF5 or equivalent |
| Magnetic stirrer | Labasco or equivalent |
| Water bath | Gant W14 or equivalent |

Instrument Settings

| UV spectrophotometer | Wavelengths | 244.259 and 274 nm |
| | Flow cell | 1.000 cm |
| Waterbath | Temperature | 37° C. |
| Secondary pump | Pump flow | 30 rpm |
| Magnetic stirrer | Rotation | Gentle stir |

Figure 1:
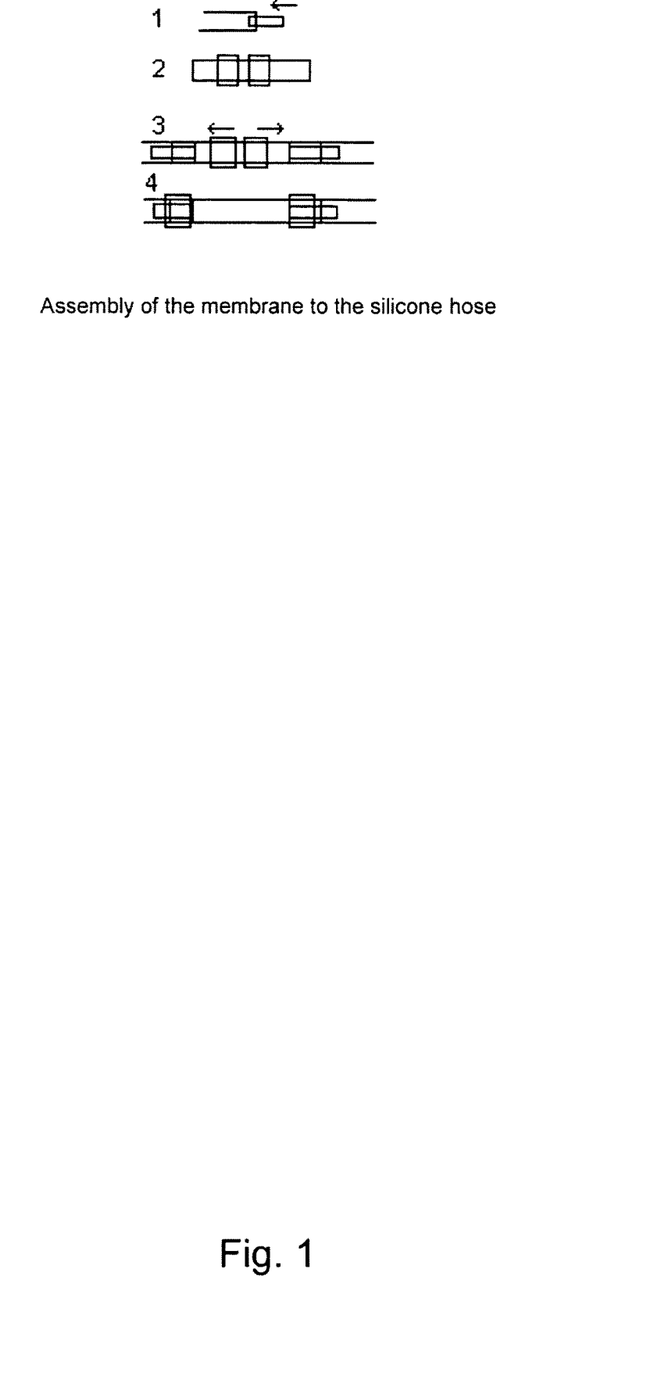
FIG. 1 shows an assembly of the dialysis membrane to the silicone hose—the assembly is a part of the dissolution testing apparatus for testing of snuff compositions

Materials
Dialysis membrane, Spectra/Por®, MWCO 500,
Silicon tubing, i.d. 6 mm
Sample tube
250 ml beaker
Reagents
Chemicals & Solvents:
Purified water, $H_2O$
Sodium Hydroxide, min 98%, NaOH
Sodium Dihydrogen Phosphate Monohydrat, min 98%, $NaH_2PO_4H_2O$
Reference Material:
Nicotine bitartrate dihydrate, standard
Solutions:
5 M Sodium hydroxide
Phosphate buffer, pH 6.8
Procedure
Apparatus Assembly Cut two pieces of silicon hoses, 150 and 35 cm long. Insert a 3 cm long hard plastic hose (o.d. 7 mm) in one end of the two 'blood vessels' for support. Cut a piece of dialysis membrane and pre-treat according to manufacturer. Thread the membrane through two 2.5 cm long silicon hose pieces (i.d. 6 mm). The supported ends of the blood vessels should be inserted approximately 3 cm into the membrane and secured with the two small silicon rings (See FIG. 1).

Add 250 ml phosphate buffer [6] to the 250 ml beaker and add a magnetic bar. Place it in the water bath and start the heating and rotation. Connect the silicone hose to the secondary pump and place the longest part to the beaker. Place a pipette tip (1 ml) into the shorter end to work as a pressure restrictor. The hole in the tip may be expanded in order to adjust the back pressure. Prime the tubing with buffer.

Figure 2:
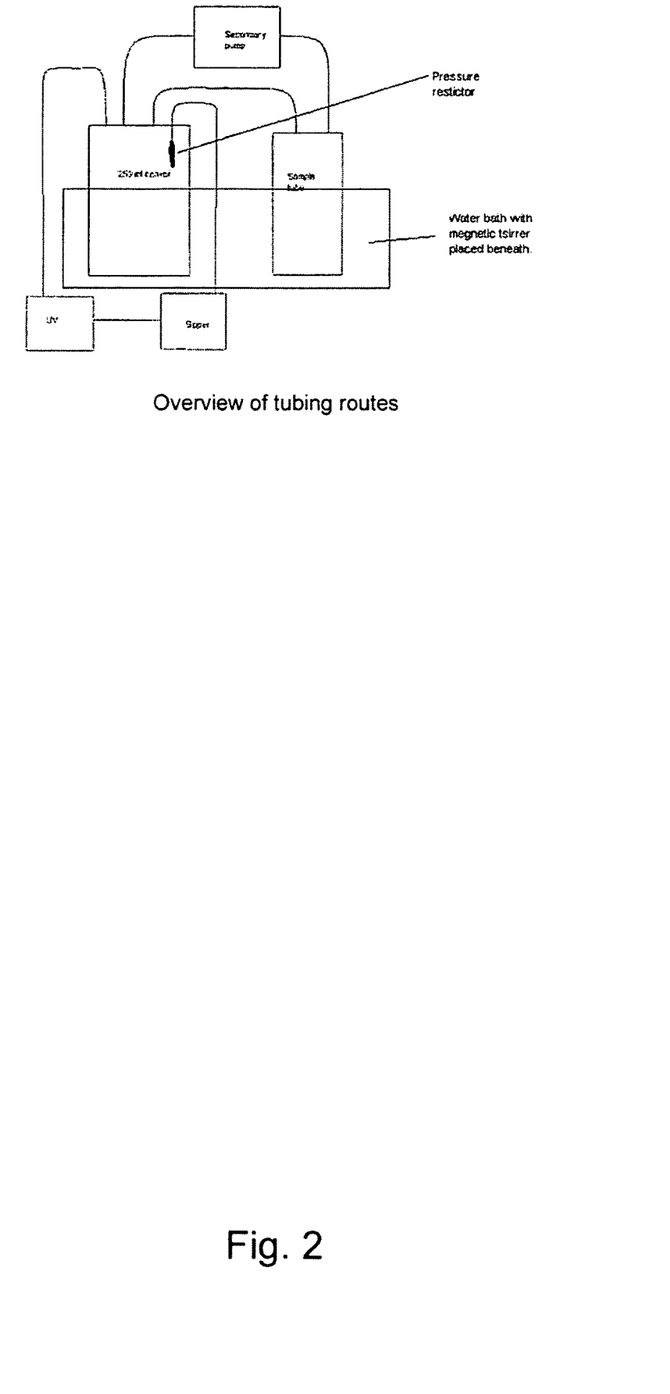
FIG. 2 shows an overview of tubing routes in the dissolution testing of snuff compositions

Place the two tubings from the flow cell in the beaker. (See FIG. 2) and obtain a blank measurement.

Figure 3:
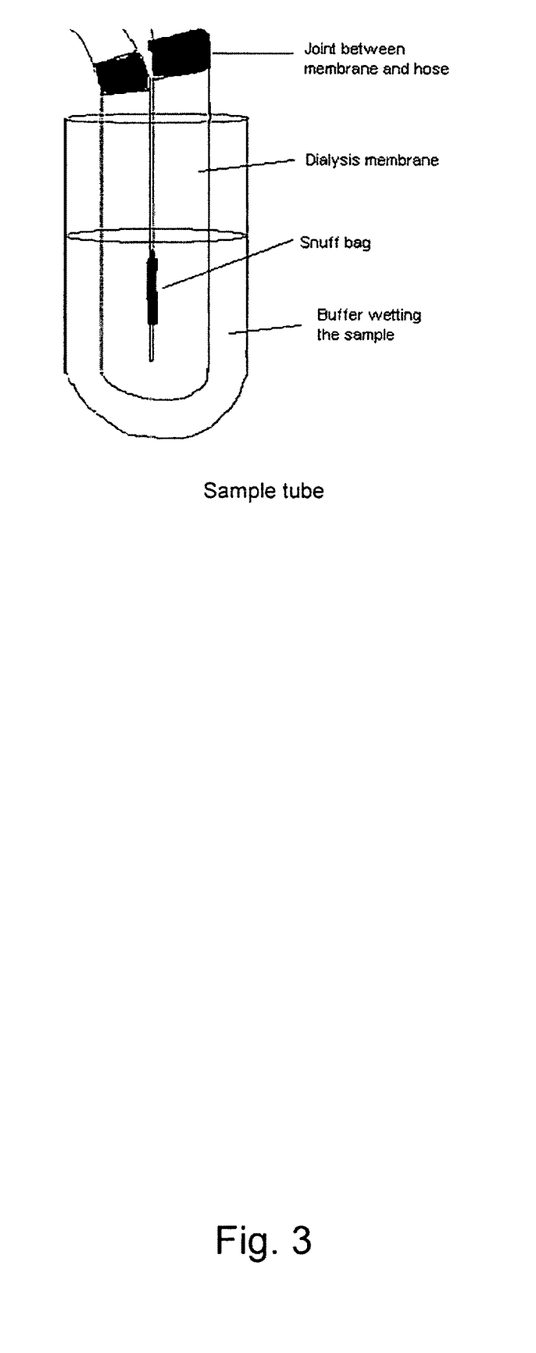
FIG. 3 shows a sample tube for dissolution testing of snuff compositions

Stop the flow and fold the membrane on the middle. Use a piece of paper to slide the membrane into the sample tube as far down as possible. Start the pump and carefully insert the snuff bag halfway down the sample tube between the membranes (see FIG. 3). Add phosphate buffer [2] to the tube enough to cover the sample. Place the sample tube in the water bath and start the analysis.

Sampling

Blank: Measure blank before the membrane is placed into the sample tube.

Sampling: Withdraw sample online every fifth minute for 30 minutes using the sipper.

Measure the absorbance at 244, 259 and 274 nm.

Standards: Pump S1-S3 into the flow cell after the sampling sequence. Measure the absorbance at 244, 259 and 274 nm.

Evaluation

The concentrations of nicotine in the samples are calculated.

As an alternative method, USP basket method (in vitro dissolution of tablets) can be used employing 500 ml water as dissolution medium.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Snuff Bag Compositions E, F, G, H, I and J

Nicotine was sorbed onto microcrystalline cellulose (MCC) as described in WO 2004/056363. Accordingly, in the present example 2.40 ml nicotine was dissolved in 25 ml ethanol (99.5%). 47.6 g MCC of type PH-102 was loaded into a high-speed mixer and the nicotine was slowly added. After vacuum drying of the obtained wetted mass a fine-grained, white powder of nicotine-microcrystalline cellulose carrier complex was obtained.

Nicotine was sorbed onto microcrystalline cellulose (MCC) to obtain nicotine-microcrystalline cellulose carrier complexes essentially as described above. The obtained nicotine-microcrystalline cellulose carrier complexes were mixed with the remaining ingredients to obtain the compositions E, F, G, H, I and J stated in the following table:

| Ingredient | Composition E Quantity (mg/unit) | Composition F Quantity (mg/unit) | Composition G Quantity (mg/unit) | Composition H Quantity (mg/unit) | Composition I Quantity (mg/unit) | Composition J Quantity (mg/unit) |
|---|---|---|---|---|---|---|
| Nicotine | 6.00 | 6.00 | 6.00 | 4.00 | 4.00 | 6.00 |
| Microcrystalline cellulose | 138 | 137 | 137 | 139 | 139 | 135 |
| Peppermint powder flavour | 6.00 | 6.00 | 6.00 | 6.00 | 6.00 | 6.00 |
| Acesulfame potassium | 0.06 | 0.06 | 0.06 | 0.06 | 0.06 | 0.06 |
| Aspartame powder | 0.06 | 0.06 | 0.06 | 0.06 | 0.06 | 0.06 |
| Sodium carbonate | — | — | — | — | — | 1.20 |
| Sodium hydrogen carbonate | — | 1.20 | — | 1.20 | — | 1.20 |
| Sodium triphosphate | — | — | 1.20 | — | 1.20 | — |
| Target Weight | 150 | 150 | 150 | 150 | 150 | 150 |
| Measured pH, 5 g in 100 ml H2O | 9.47 | 9.02 | 10.4-10.8 | 8.95 | 10.3-10.5 | 9.95 |
| In-vitro release, 30 min (mg)* | 2.6 | 2.6 | 2.6-2.7 | 1.8 | 1.6-1.7 | 3.0 |
| Measured assay | 5.9 | 6.0 | 6.0-6.3 | 4.2 | 3.8-4.2 | 6.3 |

Nicotine was purchased from Siegfried, Switzerland, (batch no. 0338I006), Microcrystalline cellulose was purchased from FMC, Belgium (batch no. M301C), Peppermint powder flavour was purchased from Firmenich, Switzerland (batch no. JP05040527), Acesulfame potassium was purchased from L&P Food Ingredient, China (batch no.

(ZD02035), Aspartame powder was purchased from NutraSweet, Switzerland (batch no. C000220), Sodium carbonate was purchased from Aldrich, Germany (batch no. A008729PI), Sodium hydrogen carbonate was purchased from Merck, Germany (batch no. K28409723047), Sodium triphosphate was purchased from Sigma, USA (supplied from Swedish Match Sweden).

150 mg of the compositions E-J, respectively, were filled into snuff bags made of a snuff bag material obtained from Swedish Match, Sweden (batch no. W-NR00217, RL-NR6). The snuff bag size used is similar to the present marketed dry snuff bags, i.e. as "Catch® dry".

Example 2

In vitro Release from Snuff Bag Compositions E, F, G, H, I and J

Measurement of in vitro release rates of nicotine from snuff bags were performed using an in vitro dissolution test developed at Swedish Match, Stockholm, and utilizing a plastic flow-chamber in a tube with buffer solution combined with UV detection on a spectrophotometer at 260 nm. The details are mentioned above under the heading "In vitro dissolution test".

The in vitro release of nicotine from compositions E-J in percentage of the total content of nicotine are stated in the table below:

| | COMPOSITION | | | | | |
|---|---|---|---|---|---|---|
| | Composition E | Composition F | Composition G | Composition H | Composition I | Composition J |
| Nicotine content (mg) | 6.00 | 6.00 | 6.00 | 4.00 | 4.00 | 6.00 |
| In vitro release, 30 min (mg) | 2.6 | 2.6 | 2.6-2.7 | 1.8 | 1.6-1.7 | 3.0 |
| Percentage of released nicotine | 43% | 43% | 43-45% | 45% | 40-42% | 50% |

Figure 4:
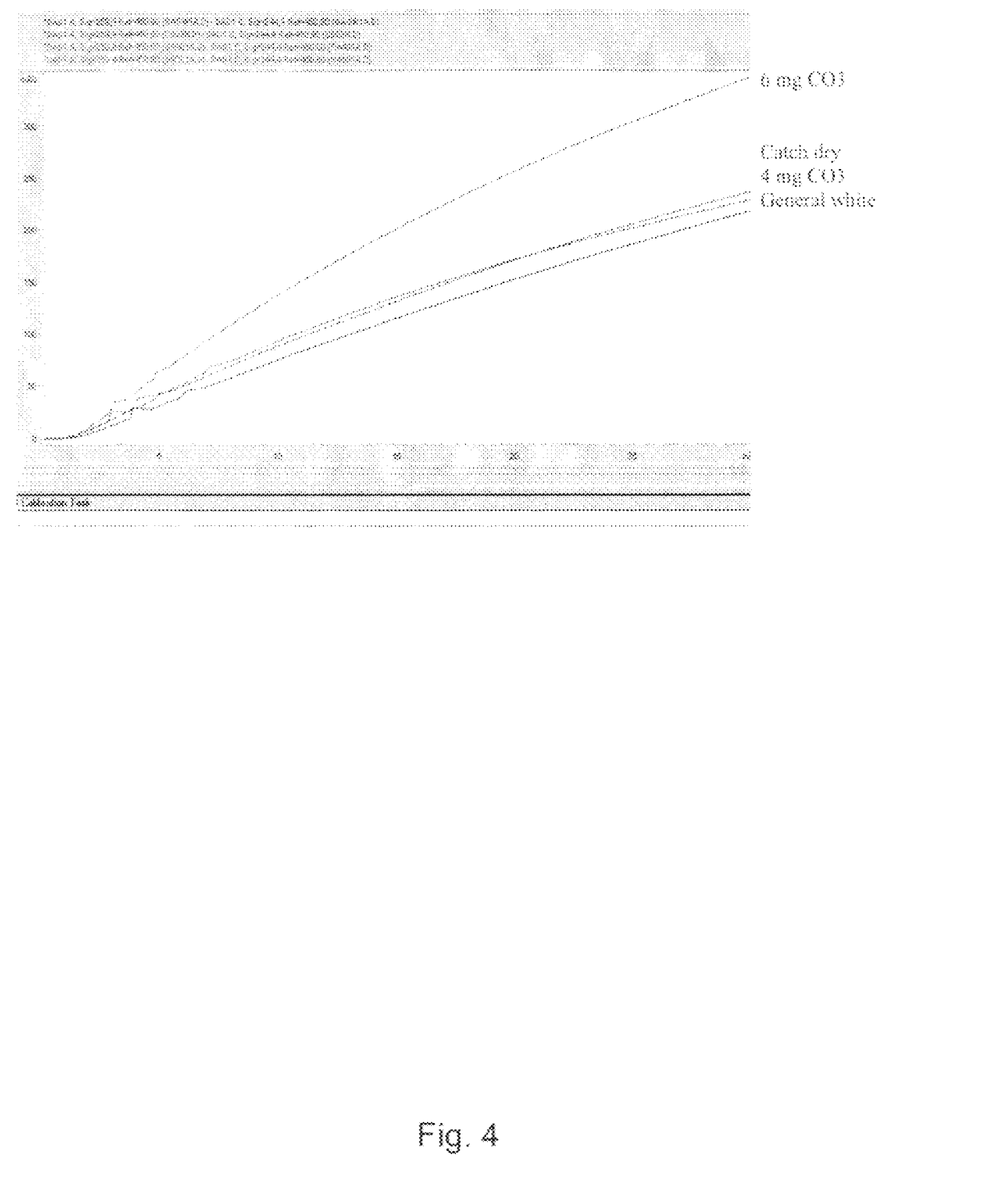
FIGS. 4 and 5 show in vitro release profile for snuff compositions described in Example 2

Furthermore, comparison studies of the in vitro release profiles of nicotine from snuff bags containing snuff compositions according to the present invention and already marketed snuff bags were performed. In FIG. 4 the in vitro release profiles of nicotine from compositions F and H were compared with the in vitro release profiles of nicotine from the present marketed dry snuff bags "Catch® dry" and "general white" using the first of the above-mentioned in vitro release methods. FIG. 4 illustrates the improved in vitro release of nicotine from snuff compositions according to the present invention compared to both "Catch® dry" and "general white": Snuff composition F which contains 6 mg nicotine releases significantly more nicotine than the already marketed products "Catch® dry" and "general white". As the marketed products are natural products information of the exact content of nicotine is not available, but it is disclosed that the weight is 1 gram or less, the nicotine content is 5-11 mg, the pH is 7.3-8.5 and the buffer content is 1.5-3.5%.

Figure 5:
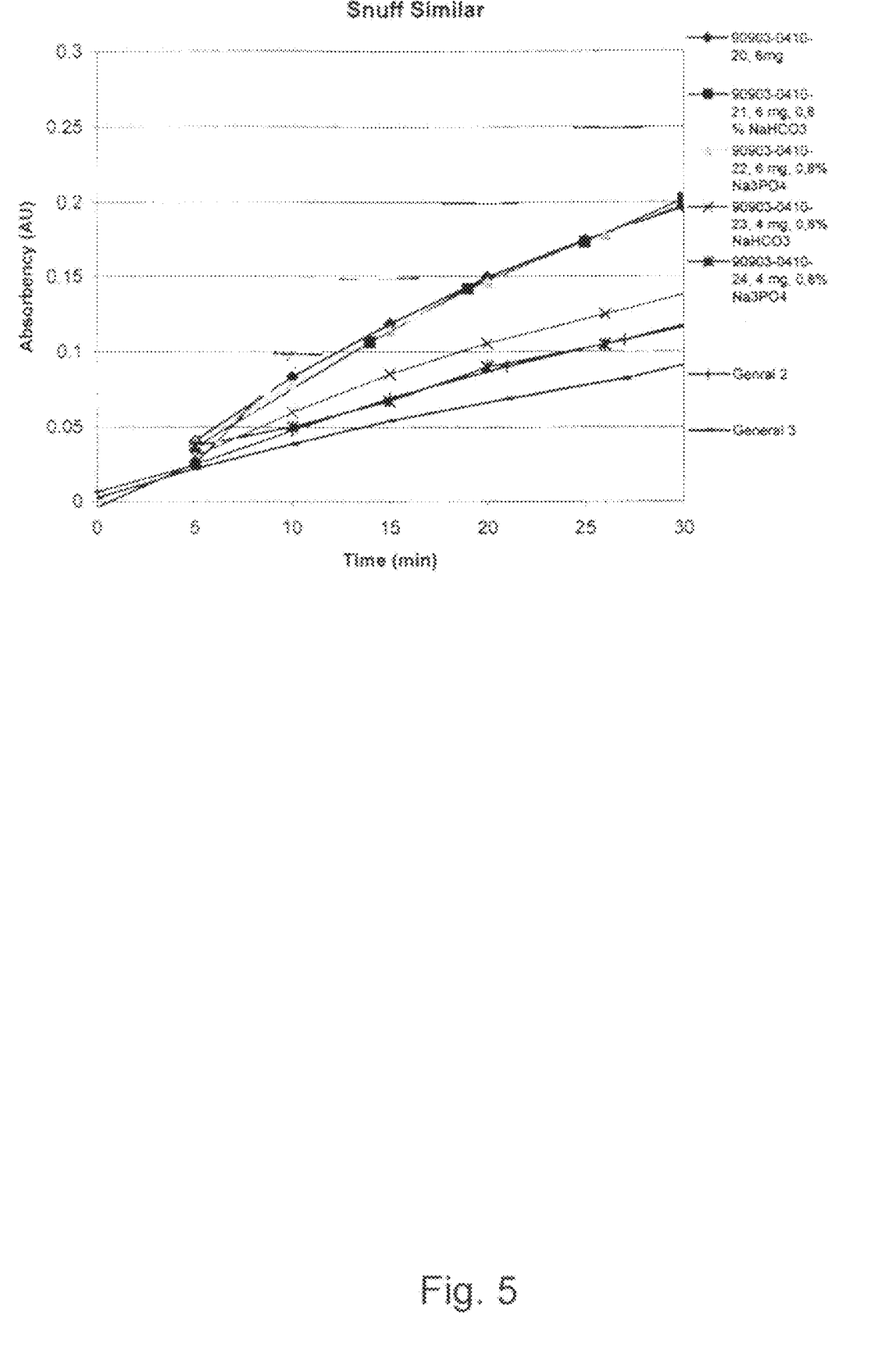

In FIG. 5 the in vitro release rates of nicotine from snuff compositions E, F and G containing 6 mg of nicotine and snuff compositions H and I containing 4 mg of nicotine, were compared to the in vitro release rates of nicotine from "General" compositions 1, 2 and 3. Again, the snuff compositions according to the present invention exhibit a better release relative to the total content of nicotine in the composition/product.

Example 3

In vivo Uptake of Nicotine from Snuff Bag Containing Composition

A comparison study of the in vivo uptake of nicotine from the snuff product "General", 4 mg Nicorette® chewing gum and a snuff bag comprising composition J was performed. Composition J contained 0.8% sodium hydrogen carbonate and 0.8% sodium carbonate. Blood samples were taken at 0, 5, 10, 15, 20, 30 and 40 minutes after application and the plasma concentrations of nicotine were determined by ABS laboratories, London, England. After addition of sodium hydroxide, the plasma samples were extracted with dichloroethane and nicotine was quantitatively determined by gas chromatography using a nitrogen/phosphorous detector. 5-methyl cotinine was used to internally standardize the procedure. The limit of quantification is 0.5 ng/ml.

Figure 6:
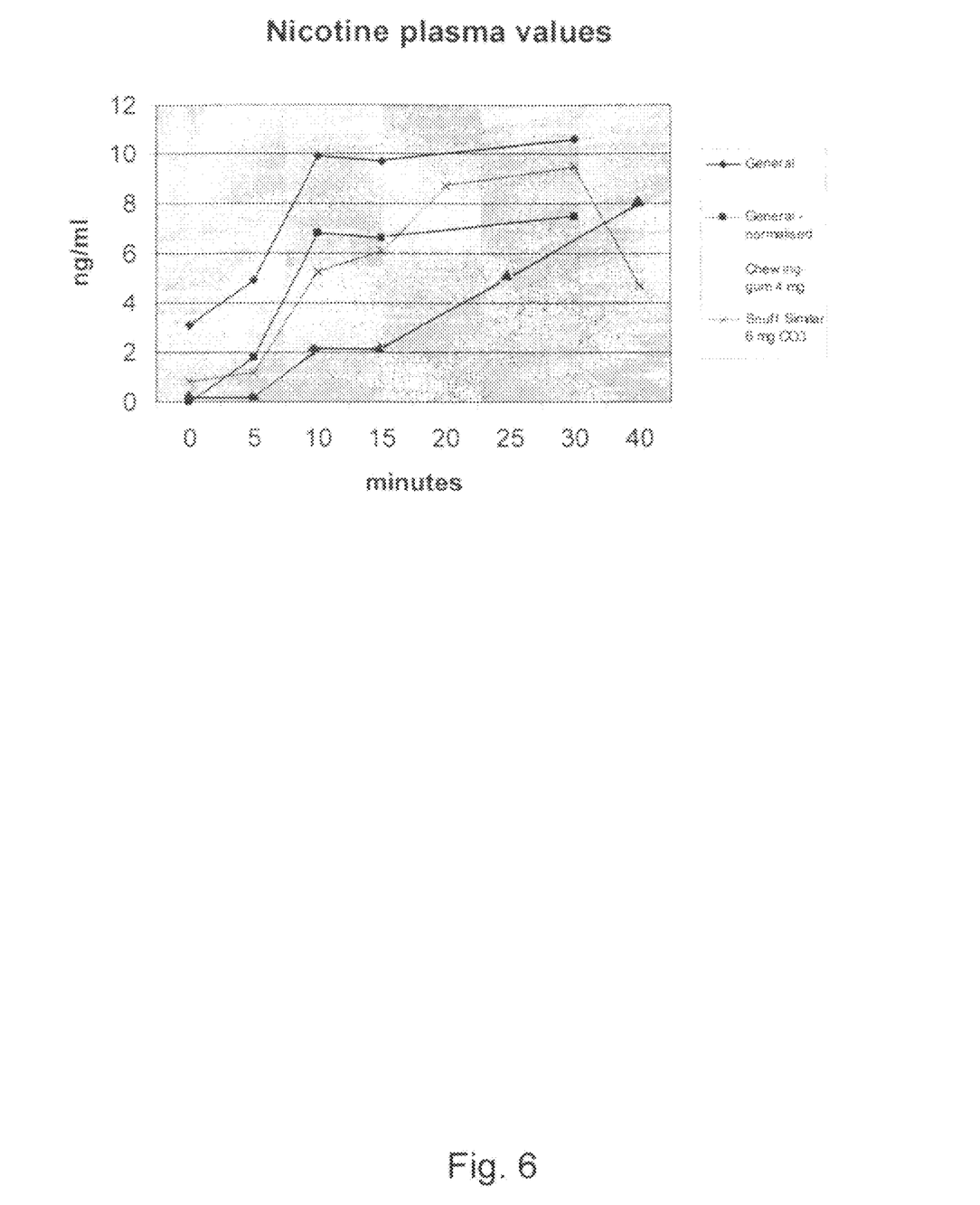
FIGS. 6 and 7 show the in vivo uptake of nicotine from snuff compositions described in Example 3.

The results are shown in FIG. 6. For comparison reasons the in vivo uptake of nicotine from the snuff product "General" was normalized to a nicotine content of 6 mg. FIG. 6 shows that over a time period of 30 minutes, the snuff bag containing composition J provides a plasma level of nicotine exceeding those of both "General" and Nicorette® 4 mg nicotine chewing gum.

Figure 7:
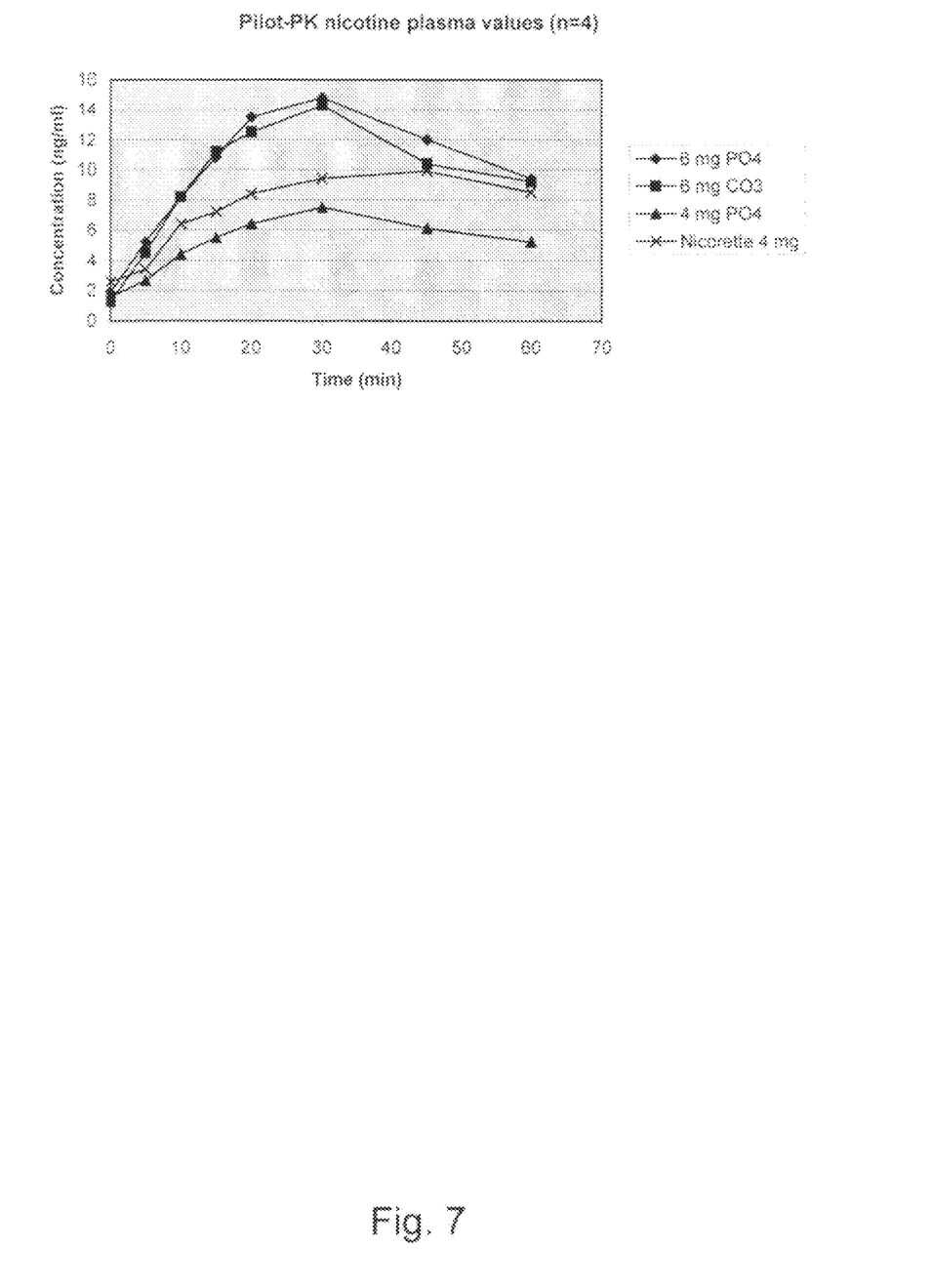

Furthermore, a pilot pharmacokinetic study (n=4) in which the in vivo uptake of nicotine from snuff compositions G, J and I were compared to the in vivo uptake from Nicorette® 4 mg chewing gum. The result shown in FIG. 7 illustrates that the in vivo uptake of nicotine from each of these snuff compositions is significantly better than from Nicorette® 4 mg chewing gum.

Example 4

Residual Amounts of Nicotine in Snuff Bags Comprising Snuff Compositions G, I and J —in vitro vs. in vivo Snuff bags comprising either of compositions G, I or J were subjected to either the above-mentioned in vitro dissolution test employing USP basket apparatus or the above-mentioned pilot pharmacokinetic assay in 30 minutes. Subsequently, the residual nicotine content in the snuff bags was investigated using a dissolution bath combined with a UV-detection on a spectrophotometer at 260 nm. The dissolution was determined according to the dissolution method for tablets USP (basket) using 500 ml water as dissolution medium and a temperature of 37° C.

The results are shown in the following table:

| Snuff composition | Composition I | Composition G | Composition J |
|---|---|---|---|
| Measured nicotine assay (mg) | 3.8 | 6.3 | 6.3 |
| Mean in vitro residual amount nicotine after 30 minutes (n = 2) (mg) | 1.9 | 3.6 | 3.3 |
| Mean in vitro residual amount nicotine after 30 minutes (n = 2) (%) | 50 | 57 | 52 |
| Mean in vivo residual amount nicotine after 30 minutes (n = 4) (mg) | 1.98 | 3.06 | 2.84 |
| Mean in vivo residual amount nicotine after 30 minutes (n = 4) (%) | 52 | 49 | 45 |

-continued

| Snuff composition | Composition I | Composition G | Composition J |
|---|---|---|---|
| Diversion in vitro vs in vivo (% vs %) | −2 | +8 | +7 |

It follows from the figures in the above table, that the residual amount of nicotine in the snuff bags after 30 minutes of in vitro dissolution test is between 50% and 57% of the initial content of nicotine, i.e. between 43% and 50% of the nicotine has been released in the in vitro dissolution test. It further follows that the residual amount of nicotine in the snuff bags after 30 minutes of the in vivo pharmacokinetic study, is between 45% and 50% of the initial content of nicotine, i.e. between 45% and 50% of the nicotine has been absorbed in the bloodstream.

Example 5

Figure 8:
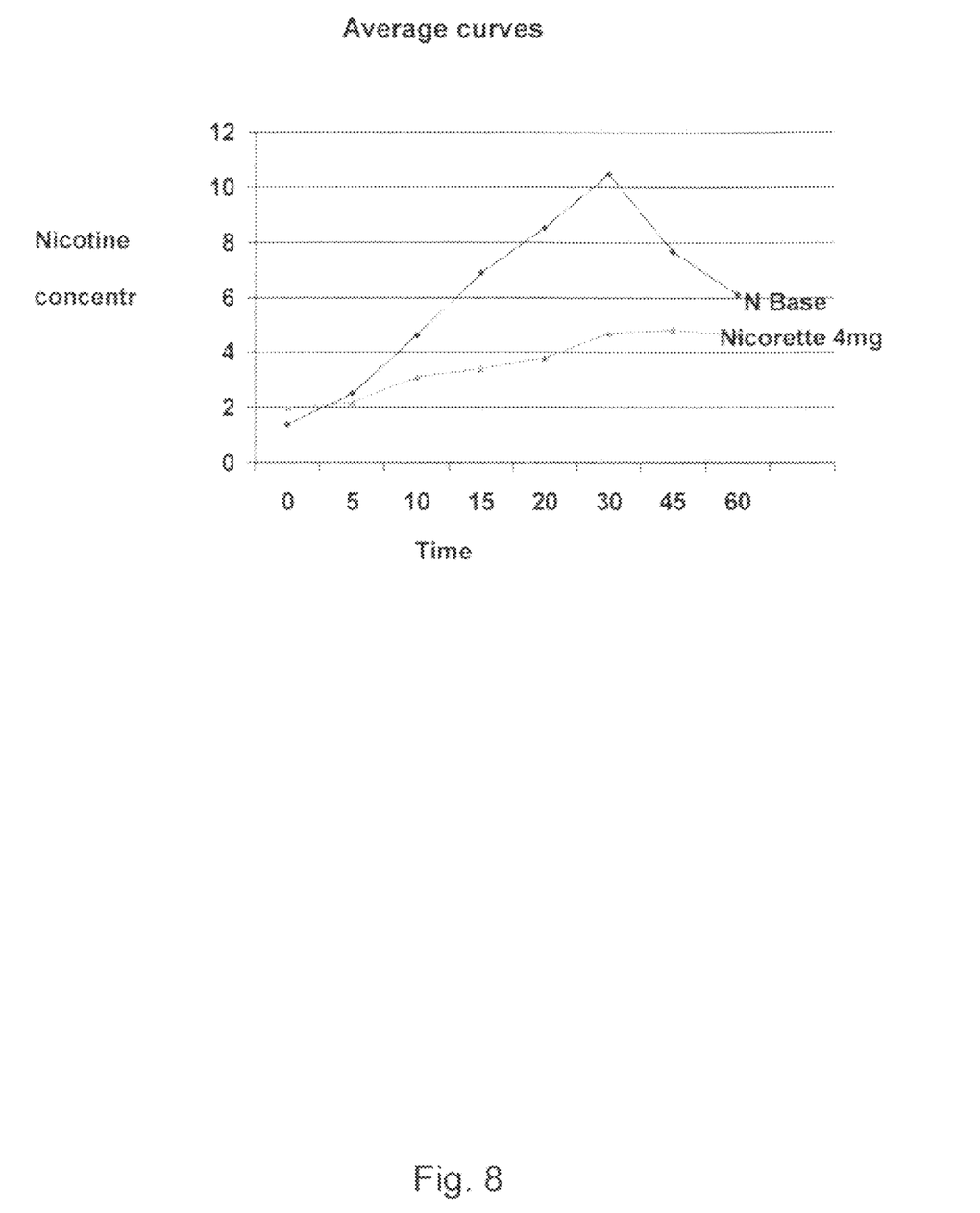
FIG. 8 show the plasma concentration versus time for the experiment described in Example 5 comparing Nicorette® chewing gum (4 mg) with a snuff composition of the invention containing 5 mg of nicotine

Comparison of Nicorette 4 mg gum with MCC-nicotine Containing Snuff Composition with 5 mg Nicotine Single dose pharmacokinetics was studied in four subjects in comparison to Nicorette 4 mg gum (FIG. 8). FIG. 8 shows the results from a single dose pharmacokinetic study in four subject comparing Nicorette® 4 mg chewing gum with a snuff composition containing MCC-nicotine corresponding to 5 mg nicotine after oral application.

The bioavailability of nicotine from the nicotine snuff composition appears higher that that seen for the Nicorefte® composition even if the different in dosage is taken into account.

References

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A nicotine-cellulose combination for the preparation of a snuff composition for achievement of a fast onset of action of nicotine after application of the snuff composition to the oral cavity of a subject, wherein
   i) the nicotine-cellulose combination is a solid material composed of a cellulose, which has sorbed an amount of nicotine in voids or pores within the cellulose,
   ii) the concentration of the nicotine-cellulose combination in the composition is from 80% to 98% w/w,
   iii) the concentration of nicotine in the composition is from about 0.1 to 10% w/w, and
   iv) the composition, when subjected to an in vitro dissolution test, about 30% or more of the total content of nicotine is released within 30 minutes, and the in vitro dissolution test being in accordance with the method described herein under the heading "In vitro dissolution test", subheading "Snuff".

2. The composition of claim 1 wherein the composition has a high release rate so that when subjected to said in vitro dissolution test about 45% or more of the total content of nicotine is released within 30 minutes.

3. The composition of claim 1 wherein the nicotine-cellulose combination is enclosed in a membrane material.

4. The composition of claim 3 wherein the membrane is a natural, synthetic, semi-synthetic hydrophilic or hydrophobic membrane.

5. The composition of claim 3 wherein the membrane is made from one or more biocompatible and physiologically acceptable polymeric material.

6. The composition of claim 3 wherein the membrane material is selected from the group consisting of cellulose acetate and derivatives thereof, carboxymethyl cellulose, polycellulose ester, other cellulose derivatives including ethylcellulose, propylcellulose, polyethylene, polypropylene, polystyrene, polyvinyl chloride, polyvinyl acetate, polymers of methacrylates and acrylates, natural rubber, polycarbonate, polyethylene terephthalate, polyester, polyamide and nylon.

7. The composition of claim 1 wherein the nicotine is nicotine (free base) or a pharmaceutically acceptable salt, solvate, complex, or derivative thereof.

8. The composition of claim 1 wherein about 50% or more such as, e.g., about 60% or more, about 70% or more or about 75% or more of the total content of nicotine is released within 30 minutes when subjecting the composition to said in vitro dissolution test.

9. The composition of clam 1 wherein the composition—when subjected to said in vitro dissolution test—releases about 45% or more within 20 minutes.

10. The composition of claim 1 wherein the composition—when subjected to said in vitro dissolution test—releases about 20% or more within 10 minutes.

11. The composition of claim 1 wherein the composition is formulated for buccal administration.

12. The composition of claim 1 wherein the cellulose is a cellulose derived from a plant, an algae, a bacterium, a fungi, or combinations thereof.

13. The composition of claim 1 wherein the cellulose has a surface area of at least 0.7 $m^2/g$.

14. The composition of claim 1 wherein the cellulose is a crystalline cellulose including a microcrystalline cellulose.

15. The composition of claim 14 wherein said microcrystalline cellulose is synthetic or semi-synthetic celluloses, or it is derived from natural celluloses.

16. The composition of claim 1 wherein the mean particle size of the cellulose is in a range of from about 15 to about 250 µm.

17. The composition of claim 1 wherein the mean particle size of the microcrystalline cellulose is at the most about 500 µm.

18. The composition of claim 1 wherein nicotine is present in the composition in a concentration from about from about 0.1% w/w to about 8% w/w calculated as free base.

19. The composition of claim 1 wherein the nicotine-cellulose combination is present in a concentration from about 85% w/w to about 98% w/w.

20. The composition of claim 1 wherein the composition further Comprises one or more sweeteners in a concentration from about 0.01% w/w to about 0.2% w/w.

21. The composition of claim 1 wherein the composition further comprises one or more flavouring agents.

22. The composition of claim 21 wherein the concentration of the one or more flavouring agents in the composition is from about 1% w/w to about 15% w/w.

23. The composition of claim 21 wherein the composition further comprises one or more buffering agents.

24. The composition of claim 23 wherein the concentration of the one or more buffering agents in the composition is from about 0.1% w/w to about 5% w/w.

25. A snuff composition comprising a nicotine-cellulose combination and one or more acceptable excipients, wherein
   i) the nicotine-cellulose combination is a solid material composed of a cellulose, which has sorbed an amount of nicotine in voids or pores within the cellulose,
   ii) the concentration of the nicotine-cellulose combination in the composition is from 80% to 98% w/w,
   iii) the concentration of nicotine in the composition is from about 0.1 to 10% w/w, and
   iv) the composition, when subjected to an in vitro dissolution test, about 30% or more of the total content of nicotine is released within 30 minutes, and the in vitro dissolution test being in accordance with the method described herein under the heading "In vitro dissolution test", subheading "Snuff".

26. A snuff composition according to claim 25 wherein the composition when subjected to said in vitro dissolution test releases about 45% or more of the total content of nicotine within 30 minutes.

27. A snuff composition according to claim 26 wherein the nicotine-cellulose combination is enclosed in a membrane material.

28. A snuff composition according to claim 27 wherein the membrane is a natural, synthetic, semi-synthetic hydrophilic or hydrophobic membrane.

* * * * *